US00PP34854P2

(12) United States Plant Patent
Heus

(10) Patent No.: US PP34,854 P2
(45) Date of Patent: Dec. 20, 2022

(54) ***SCUTELLARIA* PLANT NAMED 'APPALACHIAN BLUES'**

(50) Latin Name: ***Scutellaria* hybrid**
Varietal Denomination: 'APPALACHIAN BLUES'

(71) Applicant: Peter Heus, Hinton, WV (US)

(72) Inventor: Peter Heus, Hinton, WV (US)

(73) Assignee: Plants Nouveau, Mobile, AL (US)

( * ) Notice: Subject to any disclaimer, the term of this patent is extended or adjusted under 35 U.S.C. 154(b) by 0 days.

(21) Appl. No.: 17/863,039

(22) Filed: Jul. 12, 2022

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
See application file for complete search history.

*Primary Examiner* — Karen M Redden
(74) *Attorney, Agent, or Firm* — Cassandra Bright

(57) ABSTRACT

A new and distinct cultivar of *Scutellaria* plant named 'APPALACHIAN BLUES' is disclosed, characterized by distinctive purple calyxes, stems, and leaf margins. Plants have controlled, herbaceous, clumping habits. Flowers are bi-colored, violet-blue and white. The new variety is a *Scutellaria*, typically produced as an ornamental plant.

2 Drawing Sheets

Figure 1:
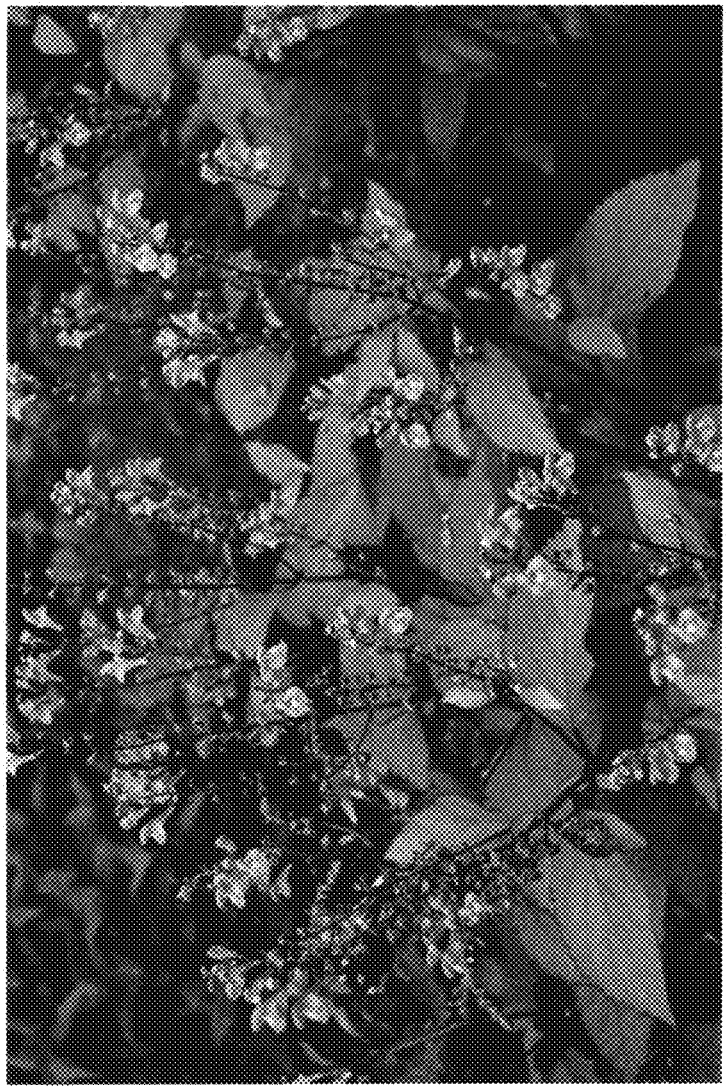

Latin name of the genus and species: *Scutellaria* hybrid. Variety denomination: 'APPALACHIAN BLUES'.

BACKGROUND OF THE INVENTION

The new *Scutellaria* cultivar is a product of a planned breeding program conducted by the inventor. The crossing resulting in this new variety was made in 2015, at a nursery in Summers County, W. Va.

The seed parent is an unidentified, unpatented variety *Scutellaria incana*. The pollen parent is an unidentified, unpatented variety *Scutellaria serrata*. The new variety was identified and selected as a potentially interesting selection in May of 2016, at the same nursery in Summers County, W. Va.

Asexual reproduction of the new cultivar 'APPALACHIAN BLUES' was first performed during the Summer of 2016 in Summers County, W. Va., by vegetative cuttings. Subsequent propagation has shown that the unique features of this cultivar are stable and reproduced true to type in successive generations.

SUMMARY OF THE INVENTION

The cultivar 'APPALACHIAN BLUES' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'APPALACHIAN BLUES'. These characteristics in combination distinguish 'APPALACHIAN BLUES' as a new and distinct *Scutellaria* cultivar:

1. Controlled plant growth.
2. Bi-color flowers (violet-blue and white).
3. Distinctive purple calyxes, stems, and leaf margins.

PARENT COMPARISONS

Plants of the new cultivar 'APPALACHIAN BLUES' are similar to the seed parent in most horticultural characteristics. However, characteristics of the new cultivar differ in the following:

1. The new variety has smaller leaves than the seed parent.
2. The new variety has larger flowers than the seed parent.
3. The new variety has purple stems and leaf margins, while the seed parent has burgundy stems and leaf margins.
4. The new variety has a shorter, bushier habit than the seed parent.
5. The new variety blooms earlier than the seed parent.

Plants of the new cultivar 'APPALACHIAN BLUES' are similar to the pollen parent in most horticultural characteristics. However, characteristics of the new cultivar differ in the following:

1. The new variety is a taller plant than the pollen parent.
2. The new variety is a more branched, bushier plant than the pollen parent.
3. The new variety produces many more flowers than the pollen parent.
4. The new variety has a later blooming period than the pollen parent.
5. The new variety has a longer blooming period than the pollen parent.

COMMERCIAL COMPARISON

Plants of 'APPALACHIAN BLUES' are similar in most horticultural characteristics to the variety *Scutellaria montana* 'Blue Sky', unpatented. The new variety, however, differs in the following:

1. Flowers of the new variety are mainly blue, with white centers; flowers of 'Blue Sky' are white with blue lips.

2. Foliage of the new variety has a maroon margin not found on this comparator.
3. Stems of the new variety are deep purple; stems of this comparator are green.

BRIEF DESCRIPTION OF THE PHOTOGRAPHS

The accompanying photograph in FIG. 1 illustrates in full color a typical plant of 'APPALACHIAN BLUES' grown outdoors in West Newbury, Mass. This plant is approximately 2-3 years old, shown in the ground.

Figure 2:
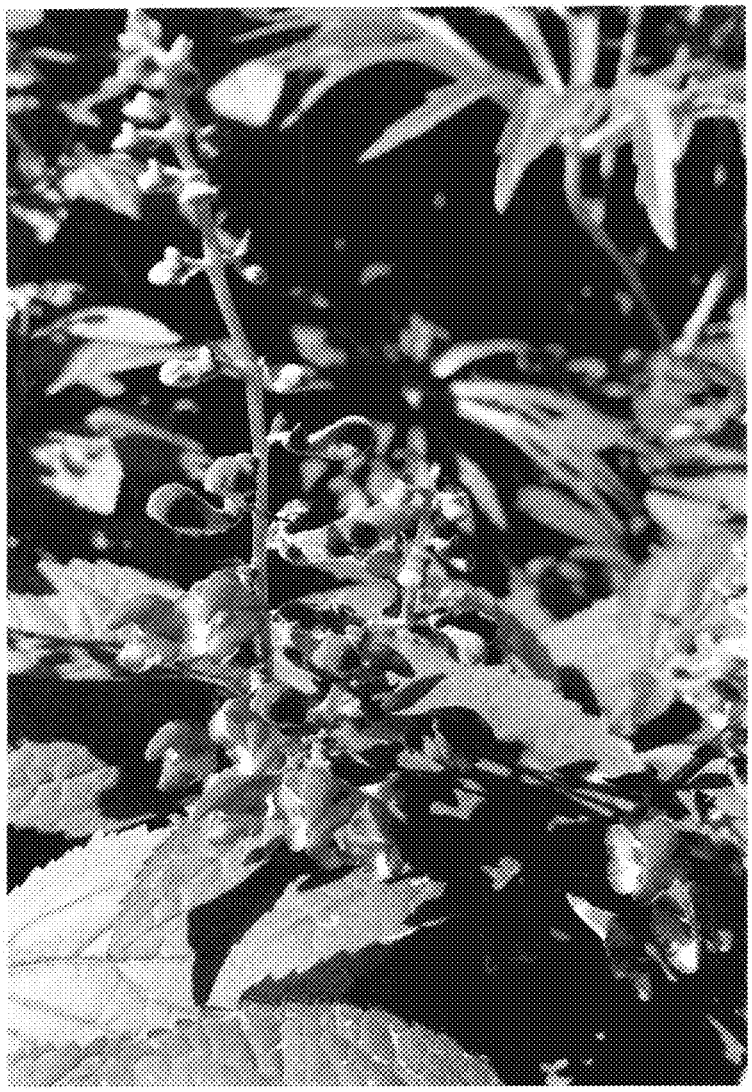

FIG. 2 illustrates a closer view of the foliage and flowering bracts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'APPALACHIAN BLUES' plant. This plant was grown outdoors in West Newbury, Mass. The plant described is approximately 5 years old. Temperatures ranged from 5-18° C. at night and 15° C. to 32° C. during the day. No artificial light, photoperiodic treatments were given to the plants. Measurements and numerical values represent averages of typical plant types.

Botanical classification: *Scutellaria* hybrid 'APPALACHIAN BLUES'.

PROPAGATION

Type of propagation typically used: Terminal vegetative cuttings.

Time to initiate roots: About 2.0 to 30 days at approximately 15° C.

Root description: Fine and fibrous, creamy white, not accurately measured with a color chart.

PLANT

Age of plant described: Approximately 5 years.

Container size of the plant described: Planted in the ground in Massachusetts in USDA hardiness Zone 6A.

Growth habit: Herbaceous perennial, clumping habit.

Height: Approximately 30 cm.

Plant spread: 60 cm.

Growth rate: Moderate.

Length of primary stem: 30 cm.

Characteristics of main stem:

- *Form*.—Square.
- *Diameter*.—About 0.3 cm.
- *Color*.—RHS Yellow-Green 144A with an RHS Greyed-Purple N186C overlay as it matures.
- *Texture*.—Glabrous.
- *Strength*.—Moderate to strong.

Branching characteristics: Free branching, basal and lateral branches. Pinching is not required but increases branching.

Length of primary lateral branches: Average 35 cm.

Diameter of lateral branches: 3 mm.

Quantity of primary lateral branches: 35-40.

Length of primary lateral branches: 30-35 cm.

Characteristics of primary lateral branches:

- *Form*.—Basal clump.
- *Diameter*.—0.4 cm.
- *Color*.—RHS Yellow-Green 146B flushed with Greyed-Purple 183B.
- *Texture*.—Glabrous.
- *Strength*.—Moderate to strong.

Internode length: 3.3 cm.

FOLIAGE

Leaf:

- *Type*.—Simple.
- *Arrangement*.—Opposite.
- *Average length*.—Approximately 13 cm.
- *Average width*.—Approximately 3.5 cm.
- *Shape of blade*.—Oblong-obovate.
- *Apex*.—Acute.
- *Base*.—Cuneate.
- *Attachment*.—Petiolate.
- *Margin*.—Dentate.
- *Texture of top surface*.—Glabrous and sparsely puberulous.
- *Texture of bottom surface*.—Glabrous.
- *Appearance of top surface*.—Matte.
- *Appearance of bottom surface*.—Slightly glossy.
- *Leaf internode length*.—Approximately 3 cm.
- *Color*.—Young foliage upper side: RHS Green N137A. Young foliage under side: RHS Yellow-Green 146B. Mature foliage upper side: RHS Yellow-Green 146A. Mature foliage under side: RHS Yellow-Green 146B. Mature margin: RHS Violet-Blue N92A.
- *Venation*.—Type: Pinnate. Venation color upper side: RHS Yellow-Green 145A. Venation color under side: RHS Yellow-Green N144A.

Petiole:

- *Length*.—2.5 cm.
- *Diameter*.—1.5 mm.
- *Color upper side*.—RHS Yellow-Green 146A.
- *Color under side*.—RHS Yellow-Green 144D.

FLOWER

Natural flowering season: Summer: June to July in West Newbury, Mass. in a typical year.

Inflorescence (raceme): Verticillaster.

- *Height*.—10-12 cm.
- *Diameter*.—3.6 cm.
- *Quantity of flowers per (average range)*.—Inflorescence has 5 to 7 pairs of flowers.

Peduncle:

- *Length*.—2 cm.
- *Diameter*.—2 mm.
- *Texture*.—Smooth.
- *Color*.—RHS Yellow-Green 144A.
- *Orientation*.—Near vertical.
- *Strength*.—Medium to strong.

Individual flowers:

Flower longevity on plant: 2-3 weeks.

Bud:

- *Shape*.—Globular.
- *Length*.—2 cm.
- *Diameter*.—Tapered 1 to 1.5 cm.
- *Color*.—RHS Violet N87B.

*Petal arrangement*.—The corolla is sympetalous and typically bilabiate with 2 small, highly fused lobes forming an upper lip and 3 larger highly fused lobes forming a lower lip.

Size:

*Diameter*.—Approximately 0.9 cm. at widest point.

*Length*.—Approximately 2.6 cm.

*Persistence*.—Persistent.

*Fragrance*.—None observed.

Petals:

*Margin*.—Entire.

*Tip shape*.—Upper lip: Attenuate. Lower lip: Emarginate.

*Length*.—Upper lip: 0.9 cm. Lower lip: 0.9 cm. Tube: 1.3 cm.

*Width*.—Upper lip: 0.25 cm. Lower lip: 1.3 cm. Tube: 0.4 cm.

*Texture*.—Upper lip: Glabrous. Lower lip: Glabrous, sparsely lanate on outer surface. Tube: Glabrous.

Color:

*Upper lip*.—When opening: Inner surface: RHS Violet-Purple 92A. Outer surface: RHS Violet-Purple 92A. Fully opened: Inner surface: RHS Violet N87B. Outer surface: RHS Violet N87B. Fading: Inner surface: RHS Violet-Blue 92C. Outer surface: RHS Violet-Blue 92B.

Color:

*Lower lip*.—When opening: Inner surface: RHS White 155C with Violet-Blue 92A markings. Outer surface: RHS White 155C with Violet-Blue 92A markings. Fully opened: Inner surface: RHS White 155C with Violet-Blue N87B markings. Outer surface: RHS White 155C with Violet-Blue N87B markings. Fading: Inner surface: RHS Violet-Blue 92A with White 155C blotch. Outer surface: RHS Violet-Blue 92A.

Color:

*Tube*.—When opening: Inner surface: RHS Violet-Blue 92C. Outer surface: RHS Violet-Blue 92A. Fully opened: Inner surface: RHS Violet-Blue 92C. Outer surface: RHS Violet-Blue 92A. Fading: Inner surface: RHS Violet-Blue 92C. Outer surface: RHS Violet-Blue 92B.

Sepals:

*Shape*.—Quantity per flower: 3 — basally fused.

*Length*.—Approximately 0.7 cm.

*Width*.—Approximately 0.2 cm.

*Margin*.—Entire.

*Texture*.—Waxy.

*Color*.—RHS Purple N79B.

Pedicels:

*Length*.—0.2 cm.

*Diameter*.—0.1 cm.

*Angle*.—About 60° to the lateral branch.

*Strength*.—Moderate.

*Texture*.—Glabrous.

*Color*.—RHS Greyed-Purple 187B.

REPRODUCTIVE ORGANS

Stamens:

*Number*.—4.

*Filament*.—2.5 cm long, white/translucent.

Anthers:

*Shape*.—Reniform.

*Length*.—Less than 0.1 cm.

*Color*.—RHS Grey-Brown N199A.

*Pollen*.—Color: RHS Greyed-Purple N187. Quantity: Very sparse.

Pistil:

*Number*.—1.

*Length*.—2.6 cm.

*Style*.—Length: Less than 0.1 cm. Color: White, not accurately measured with R.H.S. chart.

*Stigma*.—Shape: Filiform. Color: RHS Yellow-Green 144B. Ovary Color: RHS Yellow-Green N144C.

OTHER CHARACTERISTICS

Fruit/seeds: Not observed.

Disease/pest resistance: No resistance nor susceptibility to normal diseases and pests of *Scutellaria* have been observed.

Temperature tolerance: Observed cold hard to −23° C.

Drought tolerance: Drought resistance observed.

What is claimed is:

1. A new and distinct cultivar of *Scutellaria* plant named 'APPALACHIAN BLUES' as herein illustrated and described.

* * * * *